United States Patent
Kleuss et al.

(10) Patent No.: US 10,280,424 B2
(45) Date of Patent: May 7, 2019

(54) COVALENTLY CLOSED NON-CODING IMMUNOMODULATORY DNA CONSTRUCT

(71) Applicant: Mologen AG, Berlin (DE)

(72) Inventors: Christiane Kleuss, Berlin (DE); Kerstin Kapp, Berlin (DE); Burghardt Wittig, Berlin (DE); Matthias Schroff, Berlin (DE)

(73) Assignee: Mologen AG, Berlin (DE)

( * ) Notice: Subject to any disclaimer, the term of this patent is extended or adjusted under 35 U.S.C. 154(b) by 0 days.

(21) Appl. No.: 14/899,601

(22) PCT Filed: Feb. 18, 2015

(86) PCT No.: PCT/EP2015/053396
§ 371 (c)(1),
(2) Date: Dec. 18, 2015

(87) PCT Pub. No.: WO2015/124614
PCT Pub. Date: Aug. 27, 2015

(65) Prior Publication Data
US 2016/0348114 A1    Dec. 1, 2016

(30) Foreign Application Priority Data
Feb. 18, 2014   (GB) .................................. 1402847.6

(51) Int. Cl.
*C12N 15/117*     (2010.01)
*A61K 39/39*      (2006.01)
*A61K 48/00*      (2006.01)
*A61K 39/00*      (2006.01)

(52) U.S. Cl.
CPC ............ *C12N 15/117* (2013.01); *A61K 39/39* (2013.01); *A61K 48/00* (2013.01); *A61K 2039/55561* (2013.01); *C12N 2310/17* (2013.01); *C12N 2310/532* (2013.01); *C12N 2320/31* (2013.01)

(58) Field of Classification Search
None
See application file for complete search history.

(56) References Cited

U.S. PATENT DOCUMENTS

| | | |
|---|---|---|
| 2003/0050263 A1 | 3/2003 | Krieg et al. |
| 2007/0049546 A1 | 3/2007 | Brzezicha et al. |
| 2009/0053250 A1 | 2/2009 | Wittig et al. |
| 2016/0348114 A1* | 12/2016 | Kleuss |

FOREIGN PATENT DOCUMENTS

| | | |
|---|---|---|
| WO | 2001007055 | 2/2001 |
| WO | 2004/000873 A2 | 12/2003 |
| WO | 2005/063280 A1 | 7/2005 |
| WO | 2005/080567 A1 | 9/2005 |
| WO | 2006/015560 A1 | 2/2006 |
| WO | 2007/131495 A2 | 11/2007 |

OTHER PUBLICATIONS

Schmidt M., et al., "Immune-modulatory function of CPG sequence motifs in covalently-closed, double-stem-loop DNA constructs (DSLIM)," Session Type; Poster Session 60-111, Blood, American Society of Hematology, U.S., vol. 102, No. 11; Nov. 16, 2003, molecular therapy, Nature publishing.

Hagner, et al., "Covalently-closed, Dumbbell-shaped double-stem-loop DNA sonstructs ( dSLIM) with specific immunomodulatory function, molecular therapy," Nature publishing group; vol. 9, May 1, 2004, pp. 244-245.

Schmidt et al., "dSLIM Immunomodulators induce anti-tumor responses both in vitro an in vivo," Molecular Therapy, vol. 13, supplement 1, May 2006; p. S164.

Nobutaka Hanagata, "Structure-dependent immunostimulatory effect pf CpG oligodeoxynucleotides and their delivery system," International Journal of Nanomedicine, vol. 7, 2012, pp. 2181-2195.

Hartmann G et al., "Delineation of a CpG phosphorothioate oligodeoxynucleotide for activating primate immune responses in vitro and in vivo," The Journal of Immunology, The American Association of Immunologists, U.S., vol. 164, No. 3, 2000, pp. 1617-1624.

Schmidt, M. et al, "Cytokine and Ig-production by CG-containing sequences with phosphorodiester backbone and dumbbell-shape," Allergy, vol. 61, pages 56-63 (2006).

Krieg, A. M, "Therapeutic potential of Toll-like receptor 9 activation," Nature Rev. Drug Disc., vol. 5, 2006, pp. 471-484.

* cited by examiner

*Primary Examiner* — Michael D Burkhart
(74) *Attorney, Agent, or Firm* — Sughrue Mion, PLLC

(57) ABSTRACT

The present invention relates to a covalently closed DNA construct, a pharmaceutical composition and a vaccine and their use for the modulation of the immune system. It provides a DNA construct for immunomodulation comprising a specific DNA sequence.

5 Claims, 3 Drawing Sheets

Specification includes a Sequence Listing.

Figure 1

SEQUENCE LISTING

<160> NUMBER OF SEQ ID NOS: 4

<210> SEQ ID NO 1
<211> LENGTH: 58
<212> TYPE: DNA
<213> ORGANISM: Artificial Sequence
<220> FEATURE:
<223> OTHER INFORMATION: 30L204

<400> SEQUENCE: 1
aggtggtaac ccctaggggt taccaccttc atcgtcgttt tgtcgttttg tcgttctt        58

<210> SEQ ID NO 2
<211> LENGTH: 58
<212> TYPE: DNA
<213> ORGANISM: Artificial Sequence

```
<220> FEATURE:
<223> OTHER INFORMATION: dSLIM

<400> SEQUENCE: 2
aggtggtaac ccctaggggt taccaccttc attggaaaac gttcttcggg gcgttctt     58

<210> SEQ ID NO 3
<211> LENGTH: 24
<212> TYPE: DNA
<213> ORGANISM: Artificial Sequence
<220> FEATURE:
<223> OTHER INFORMATION: ODN2006 linear PTO

<400> SEQUENCE: 3
tcgtcgtttt gtcgttttgt cgtt     24

<210> SEQ ID NO 4
<211> LENGTH: 58
<212> TYPE: DNA
<213> ORGANISM: Artificial Sequence
<220> FEATURE:
<223> OTHER INFORMATION: ODN2006 PTO in Loops

<400> SEQUENCE: 4
aggtggtaac ccctaggggt taccaccttc atcgtcgttt tgtcgttttg tcgttctt     58
```

COVALENTLY CLOSED NON-CODING IMMUNOMODULATORY DNA CONSTRUCT

The sequence listing electronically filed herewith is hereby incorporated by reference in its entirety (File Name: 2015-12-18_Sq_List.TXT; File Size: 1KB; Date Created: Dec. 17, 2015.)

FIELD OF THE INVENTION

The present invention relates to a covalently closed DNA construct, a pharmaceutical composition and a vaccine and their use for the modulation of the immune system.

BACKGROUND OF THE INVENTION

The term "immunotherapy" defines the treatment of diseases by inducing, enhancing or suppressing an immune response. The strategy of immunotherapies is to fight diseases, such as cancer, infectious diseases, allergy and asthma.

A variety of active agents, so called immunomodulators, that can be used in immunotherapy are known. Specific DNA sequences belong to those known immunomodulators. Most known immunomodifying short DNA sequences contain an unmethylated cytosine guanine motif (CG motif), which has been described by Krieg et al. (Nature 1995 374: 6522 546-549). The occurrence of unmethylated CG motifs is substantially suppressed in the genome of eukaryotes compared to prokaryotes or viruses. Therefore, DNA molecules containing such a motif have evolved as a natural "danger signal" and trigger the immune system in the fight against prokaryotic or viral pathogens. This can be exploited therapeutically or prophylactically by using such sequences to treat or prevent infectious with immunotherapy.

DNA constructs comprising unmethylated CG motifs are able to elicit a considerable physiological effect by strongly stimulating effector cells of the innate immune system including dendritic cells, macrophages, natural killer (NK) and NKT cells. Unmethylated CG motifs are detected by the innate immune pattern recognition receptor Toll-like receptor (TLR) 9. While the exact recognition mechanism is not yet fully understood, significant progress in unraveling the underlying pathways has been made (A. Krieg, Nat. Rev. Drug Disc., 5:471-484, 2006).

It is assumed that upon binding of DNA constructs containing unmethylated CGs to the receptor, multiple signal cascades are activated in responding cells. By upregulation of characteristic surface molecules and secretion of cytokines, adaptive immunity with a predominant Th1 pattern is induced. Such constructs can be used in combination with, for example, antibodies, chemotherapy or radiation therapy, vaccines or cytokines. Allergic diseases and asthma are mostly Th2-mediated. By increasing the ratio of Th1/Th2, the Th2-mediated responses are attenuated and thereby these types of diseases can be treated or prevented.

Surface molecules, which are upregulated by the TLR-9 pathway, include, for example, CD40, CD69, CD80, CD86 or CD169, depending on the cell type. The enhanced secretion of cytokines is also characteristic for distinct cell types; cytokines include, for example, macrophage inflammatory proteins (MIP)-1alpha, MIP-1beta, interleukin (IL)-6, IL-8, interferon (IFN)-alpha, tumor necrosis factor (TNF)-alpha, IFN-gamma, monocyte chemotactic protein (MCP)-1 or IFN-gamma-induced protein of 10 kDa (IP-10).

In order to prevent or treat diseases, vaccination has been proven as a very effective approach. To ensure a strong and durable immune response, adjuvants capable of stimulating antigen-presenting cells such as dendritic cells, are usually administered together with the antigen, and for that purpose TLR9 agonists have been shown to be potent immunostimulants.

Preclinical and ongoing clinical studies support the use of TLR-9 agonists as immunomodulators and/or adjuvants, and proof their anti-tumor effect by enhancing both the humoral and cellular responses.

Independently of any explanations of the underlying mechanisms by which unmethylated CG motifs influence or modulate an immune response, many approaches were developed for modulation of the immune system by using such motifs. The WO 1998/018810 discloses that immunostimulatory sequences containing unmethylated CG motifs are even more effective when they are part of a single strand. However, administering an open-chained single-stranded DNA molecule is not practicable due to the quick degradation of single-stranded nucleic acids. Consequently, different methods for the protection of single- or double-stranded DNA constructs comprising an unmethylated CG motif were developed.

To achieve resistance against the degradation by DNA nucleases the phosphodiester bonds in the backbone of a nucleic acid polymer are frequently modified to phosphorothioates. Besides a somewhat less stimulatory activity of such phosphorothioate-protected nucleic acids clinical trials within the last years showed that the toxicity of a phosphorothioate-protection exclude or severely limit such nucleic acids from any use in pharmaceutical compositions or medicaments.

From the 4 classes of known activators with distinct immunomodulation profiles all members except one comprise of linear DNA molecules. The exception is disclosed in EP 1 196 178. This document discloses short deoxyribonucleic acid molecules, comprising a partially single-stranded, dumbbell-shaped, covalently closed sequence of nucleotide residues comprising CG motifs ("dSLIM") consisting entirely of natural DNA. According to the disclosure of the EP 1 196 178 the CG motifs are located within the single-stranded loops at both ends of the double-stranded stem of the disclosed molecule or within the double-stranded stem. The single-stranded hairpin loops protect a double-stranded stem from degradation by DNA nucleases within or outside of the cell. Document US 2009/0053250 A1 discloses such dumbbell-shaped, covalently closed molecules comprising CG motifs in combination with chemotherapeutic drugs. US 2007/0049546 A1 discloses the dumbbell-shaped, covalently closed molecules comprising CG motifs with covalently attached one or more substituents. The publication "Schmidt M. et al., 2006, "Cytokine and Ig-production by CG-containing sequences with phosphorodiester backbone and dumbbell shape", Allergy, Vol. 61, pp. 56-63" suggests that such dumbbell-shaped, covalently closed molecules comprising certain CG motifs might be useful in the treatment of allergic diseases.

Document WO 2010/039137 discloses immune regulatory oligonucleotides as antagonists for TLR mediated diseases having one or more chemical modifications in the sequence flanking an immune stimulatory motif and/or in an oligonucleotide motif that would be immune stimulatory but for the modification. Thus, the intention of the disclosed oligonucleotides of WO 2010/039137 is to suppress an immune response caused by TLRs.

WO 2005/042018 describes new so-called C-class CpG oligonucleotides, wherein a c-class oligonucleotide is characterised by CpG sequences, generally positioned at or near the 5' end or 3' end of the molecule, and a GC-rich palindrome motif, generally positioned at or near the other end of the molecule. The document discloses variations of the palindromic sequence of a c-class DNA.

Above-cited publication "A. Krieg, Nat. Rev. Drug Disc., 5:471-484, 2006" discloses distinct classes of CpG oligodeoxynucleotides and their effects but does not disclose dumbbell-shaped, covalently closed molecules comprising CG motifs which avoid phosphorothioate modification.

WO 2004/000873 A2 also discloses phosphorothioate-modified CG-containing single-stranded DNA, which can be added to fusion peptides as an adjuvant. This document dose not disclose dumbbell-shaped, covalently closed molecules comprising CG motifs.

Likewise, US 2003/0050263 deals with CG-containing oligonucleotides in the context of the treatment of HIV infections but does not deal with dumbbell-shaped, covalently closed molecules comprising CG motifs in any sequence context.

BRIEF SUMMARY OF THE INVENTION

With regard to the state of the art it is an objective of the present disclosure to provide alternative immunomodulating DNA constructs with a high immunomodulatory potential being stable after transfer into eukaryotic cells and avoiding harmful side effects.

The present invention provides a DNA construct for immunomodulation that consists of a partially single-stranded, dumbbell-shaped, covalently closed chain of DNA residues comprising twice the partially hybridized DNA sequence of SEQ ID NO:1.

As a further embodiment of the present disclosure a construct is provided wherein a single-stranded loop comprises three CG-motifs.

The invention provides further a DNA construct wherein each CG-motif is flanked on both sides by a deoxythymidine.

It is further intended that a single stranded loop of a construct according to the invention has a pyrimidine content of at least 50%. Such a construct may have deoxythymidine as pyrimidine.

As a further embodiment the construct comprises at least one nucleotide that is modified with a functional group selected from the group comprising carboxyl, amine, amide, aldimine, ketal, acetal, ester, ether, disulfide, thiol and aldehyde groups Furthermore, the modified nucleotide can be linked to a compound selected from the group comprising peptides, proteins, carbohydrates, antibodies, lipids, micelles, vesicles, synthetic molecules, polymers, micro projectiles, metal particles, nanoparticles, or a solid phase.

Another object of the present invention is a pharmaceutical composition comprising a DNA construct as described above. The pharmaceutical composition may additionally comprise a chemotherapeutic.

A further object of the present invention is a vaccine comprising a DNA construct as described above or a pharmaceutical composition comprising said DNA construct. It is further envisaged that the vaccine may comprise the DNA construct of the present disclosure as adjuvant.

Another object of the present invention is the use of a DNA construct, a pharmaceutical composition or a vaccine for the treatment of cancer or autoimmune diseases.

The use of a DNA construct, a pharmaceutical composition or a vaccine for the modulation of the immune system is also envisaged.

DETAILED DESCRIPTION OF THE INVENTION

Within the meaning of the present disclosure the term DNA construct does not indicate a limitation of the length of the corresponding DNA sequence. The monomeric units of DNA constructs are nucleotides.

A DNA construct can be manufactured synthetically or be partially or completely of biological origin, wherein a biological origin includes genetically based methods of manufacture of DNA sequences.

A "stem" according to the present disclosure shall be understood as a DNA double strand formed by base pairing either within the same DNA molecule (which is then partially self-complementary) or within different DNA molecules (which are partially or completely complementary). Intramolecular base-pairing designates base-pairing within the same molecules and base-pairing between different DNA molecules is termed as intermolecular base-pairing.

A "loop" within the meaning of the present disclosure shall be understood as an unpaired, single-stranded region either within or at the end of a stem structure. A "hairpin" is a distinct combination of a stem and a loop, which occurs when two self-complementary regions of the same DNA molecule hybridize to form a stem with an unpaired loop. A dumbbell-shape describes a linear DNA construct with hairpins at both ends flanking a stem region. Thus, a "linear DNA construct" within the context of the present disclosure describes either a linear open-chained DNA construct comprising single and/or double-stranded DNA or a linear dumbbell-shaped DNA construct comprising single stranded loops at both ends of a double stranded DNA stem.

A "solid phase" to which the nucleotides are covalently or non-covalently attached refers to, but is not restricted to, a column, a matrix, beads, glass including modified or functionalized glass, silica or silica-based materials including silicon and modified silicon, plastics (comprising polypropylene, polyethylene, polystyrene and copolymers of styrene and other materials, acrylics, polybutylene, polyurethanes etc.), nylon or nitrocellulose, resins, polysaccharides, carbon as well as inorganic glasses, metals, nanoparticles, and plastics. Thus, microtiter plates are also within the scope of a solid phase according to the present disclosure.

Immunomodulation according to the present disclosure refers to immunostimulation and immunosuppression. Immunostimulation means preferentially that effector cells of the immune system are stimulated in order to proliferate, migrate, differentiate or become active in any other form. B cell proliferation for instance can be induced without co-stimulatory signals by immunostimulatory DNA molecules, which normally require a co-stimulatory signal from helper T-cells.

Immunosuppression on the other hand shall be understood as reducing the activation or efficacy of the immune system. Immunosuppression is generally deliberately induced to prevent for instance the rejection of a transplanted organ, to treat graft-versus-host disease after a bone marrow transplant, or for the treatment of autoimmune diseases such as, for example, rheumatoid arthritis or Crohn's disease.

In this context, immunomodulation may also refer to the influence of the nature or the character of an immune reaction, either by affecting an immune reaction which is still developing or maturing or by modulating the character of an established immune reaction.

The term "vaccination" used in this disclosure refers to the administration of antigenic material (a vaccine) to produce immunity to a disease. Vaccines can prevent or ameliorate the effects of infection by many pathogens such as viruses, fungi, protozoan parasites, bacteria but also of allergic diseases and asthma, as well as of tumors. Vaccines typically contain one or more adjuvants, e.g. immunostimulatory nucleic acids, used to boost the immune response. Vaccination is generally considered to be the most effective and cost-effective method of preventing infectious and other diseases.

The material administered can, for example, be live but weakened forms of pathogens (bacteria or viruses), killed or inactivated forms of these pathogens, purified material such as proteins, nucleic acids encoding antigens, or cells such as tumor cells or dendritic cells. In particular, DNA vaccination has recently been developed. DNA vaccination works by insertion (and expression, triggering immune system recognition) of DNA encoding antigens into human or animal cells. Some cells of the immune system that recognize the proteins expressed will mount an attack against these proteins and against cells expressing them. One advantage of DNA vaccines is that they are very easy to produce and store. In addition, DNA vaccines have a number of advantages over conventional vaccines, including the ability to induce a wider range of immune response types.

Vaccination can be used as a prophylactic approach, leading to immunity against the antigen in the vaccinated, healthy individual upon exposure to the antigen. Alternatively, a therapeutic vaccination can cause an improved response of the immune system of the vaccinated, diseased individual, by guiding the immune system of the individual towards the antigens. Both prophylactic and therapeutic vaccination can be applied to humans as well as animals.

The term "gene therapy" used in this disclosure refers to the transient or permanent genetic modification (e.g. insertion, alteration, or removal of genes) of an individual's cells and/or biological tissues in order to treat diseases, such as tumors or autoimmune diseases. The most common form of gene therapy involves the insertion of functional genes into an unspecified genomic location in order to replace a mutated gene, but other forms involve directly correcting the mutation or modifying a normal gene that enables a viral infection or even transferring a gene or a gene fragment into a cell for its transcription.

"Autologous gene therapy" refers to using tissues or cells of the selfsame individual. The isolated cells or tissues will be modified by gene therapy and reintroduced into the donor. In contrast, "allogenic gene therapy" refers to using cells for gene therapy from an individual other than the acceptor individual. After genetic modification, the allogenic cells are introduced into the acceptor.

The term "ex-vivo gene therapy" refers to a therapy approach in which cells from an individual, e.g. hematopoietic stem cells or hematopoietic progenitor cells, are genetically modified ex vivo and subsequently introduced to the individual to be treated. The term "in-vivo gene therapy" refers to a therapy approach in which cells from an individual, e.g. hematopoietic stem cells or hematopoietic progenitor cells, are genetically modified in vivo, using viral vectors or other expression constructs for example.

Gene therapy may also be classified into "germ line gene therapy" and "somatic gene therapy". In case of "germ line gene therapy", germ cells, i.e., sperm or eggs, are genetically modified. The genetic changes are ordinarily integrated into their genomes. Therefore, the change due to therapy would be heritable and would be passed on to later generations. This approach is useful for treatment of genetic disorders and hereditary diseases. In case of "somatic gene therapy", the therapeutic genes are transferred into the somatic cells of an individual. Any modifications and effects will be restricted to the individual only, and will not be inherited by the individual's offspring or later generations.

The term "cancer" comprises cancerous diseases or a tumor being treated or prevented that is selected from the group comprising, but not limited to, mammary carcinomas, melanoma, skin neoplasms, lymphoma, leukemia, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

Autoimmune diseases according to the present disclosure comprise rheumatoid arthritis, Crohn's disease, systemic lupus (SLE), autoimmune thyroiditis, Hashimoto's thyroiditis, multiple sclerosis, Graves' disease, myasthenia gravis, celiac disease and Addison's disease.

The present disclosure provides a DNA construct for immunomodulation that consists of a partially single-stranded, dumbbell-shaped, covalently closed chain of DNA residues comprising twice the DNA sequence of SEQ ID NO:1. SEQ ID NO:1 comprises CG motifs and is also called ODN2006-loop. Two oligos of ODN2006-loop will partly hybridize and result in a dumbbell-shaped linear DNA construct. The sequence of SEQ ID NO:1 is a follows (comp FIG. 1)

5'-AGGTGGTAAC CCCTAGGGGT TACCACCTTC ATCGTCGTTT

TGTCGTTTTG TCGTTCTT-3'

The effect of CG-containing DNA constructs depends on their interaction with TLR9. As shown in the examples and figures, differences in immunomodulation profiles between classes of TLR9 agonists appear more closely related to their conformation than their individual nucleotide sequences, respectively the context of the CG-motifs.

Surprisingly, the induced stimulation pattern of a dumblell-shaped DNA construct of the present disclosure differs from the stimulation pattern induced by the corresponding linear CG oligonucleotide or even the dumbbell-shaped DNA construct disclosed in EP 1 196 178.

The induced stimulation pattern even differs unexpectedly from the pattern induced by the linear phosphorothioat protected DNA oligo ProMune (ODN2006). The sequence of ProMune is part of the single stranded loop of a DNA construct according to the present disclosure, strengthening the relevance of the context of a CG-motif containing DNA sequence.

According to the present disclosure the CG motif/s is/are located within the single-stranded and/or double-stranded region of the construct. As has been disclosed in EP 1 196 178, CG motifs are capable of eliciting an immune response whether they are included within the single-stranded or within the double-stranded region of the molecule.

The disclosure further comprises chemical modifications of at least one nucleotide with a functional group selected from the group comprising carboxyl, amine, amide, aldimine, ketal, acetal, ester, ether, disulfide, thiol and aldehyde groups. This allows coupling of the DNA construct to a compound selected from the group comprising peptides, proteins, carbohydrates, antibodies, lipids, micelles, vesicles, synthetic molecules, polymers, micro projectiles, metal particles, nanoparticles, or a solid phase by, for example, adsorption, covalent or ionic bonding. The modification can be specifically selected for the respective purpose. The construct can thereby be used, for example, to shuttle other molecules to the specific cell responding to the CG motif/s incorporated. In addition, it is possible by such modifications to couple the construct to micro projectiles which can be used to transfer the construct into the cell. The construct can also be coupled to a solid phase, e. g. a microtiter plate.

Th1-biased activation involves the activation of NK cells and cytotoxic T cells and these immune responses can be exploited for cancer therapy. Since DNA constructs containing unmethylated CG motifs preferably lead to Th1 activation, the constructs of the present disclosure can be used for treating cancer. Numerous clinical trials are ongoing involving TLR9 agonists for treatment of cancer. Such molecules have been effectively administered alone or in combination with, for example, radiation therapy, surgery, chemotherapy and cryotherapy (Krieg, J. Clin. Invest.2007 117: 1184-94). Due to their potent immunomodulation, their small size and their stability the constructs of the present disclosure are expected to be highly advantageous in this regard. In addition, their distinct immunological profile distinguishes them from other, less advantageous TLR9 ligands, and this profile can be exploited for cancer-specific treatment.

On the other hand, TLR9 agonists are also involved in the generation of regulatory T cells and can thus be used for the treatment of autoimmune diseases. The route of administration seems to be one variable determining the effect of DNA constructs containing CG motifs in vivo (Krieg, J. Clin. Invest.2007 117: 1184-94).

The immunostimulatory effect of such DNA molecules containing CG-motifs has been shown to improve the efficacy of standard therapeutical approaches such as chemotherapeutics, in cancer therapy. Therefore, pharmaceutical compositions, which comprise the constructs of the present disclosure, are also provided. Again, the advantageous features of the constructs of the present disclosure compared with the TLR9 agonists of the state of the art makes the constructs of the present disclosure promising tools for treatment of diseases such as cancer, infectious diseases, allergies and asthma. The treatment of allergies and asthma (mostly Th2-mediated) thereby benefits from the preference of Th1 activation.

Since TLR9 agonists have been shown to be potent adjuvants in vaccines, vaccines comprising the DNA constructs of the present disclosure are also provided. The constructs of the present disclosure comprise the relevant sequences for TLR9 stimulation without the need to introduce modifications for stabilizing the DNA, which might case side effects. The longer half-life of the molecule ensures efficient stimulation so that a strong immune response is expected.

To reveal the effect of the DNA constructs of the present disclosure, the following DNA constructs were used for experiments described herein (Table 1).

TABLE 1

Sequences used in experiments:

| SEQ ID NO: | Name | Sequence (5'-3') | Modified nucleotides/explanation of sequence |
|---|---|---|---|
| 1 | 30L204 | AGGTGGTAAC CCCTAGGGGT TACCACCTTC ATCGTCGTTT TGTCGTTTTG TCGTTCTT | Dumbbell-shaped DNA construct, ODN2006 PD sequence in Loops formed of two partially hybridized sequences |
| 2 | dSLIM | AGGTGGTAAC CCCTAGGGGT TACCACCTTC ATTGGAAAAC GTTCTTCGGG GCGTTCTT | Dumbbell-shaped DNA construct of EP 1 196 178 formed of two partially hybridized sequences |
| 3 | ODN2006-2 | TCGTCGTTTT GTCGTTTTGT CGTT | linear DNA construct, all phosphordiester bonds (PD) modified to phosphorothioates (PTO) |
| 4 | 30L210 | AGGTGGTAAC CCCTAGGGGT TACCACCTTC ATCGTCGTTT TGTCGTTTTG TCGTTCTT | Dumbbell-shaped DNA construct, ODN2006 PTO sequence in Loops formed of two partially hybridized sequences |

BRIEF DESCRIPTION OF THE FIGURES

The disclosure will be further illustrated by examples and figures without being limited to the disclosed embodiments. It shows:
FIG. 1 Sequence and structure of DNA construct 30L204
FIG. 2 Cytokine stimulation in PBMCs
FIG. 3 Stimulation of CD86 and CD169 in Monocytes, CD69 in NK cells and CD86 frequency in B cells

DETAILED DESCRIPTION OF THE FIGURES

Reference is made to EP 1 196 178 B1 describing the manufacture of a partially single-stranded, dumbbell-shaped covalently closed DNA construct. A construct of the present invention is made accordingly.

FIG. 1 shows the structure and sequence of a DNA construct according to the present disclosure.

Figure 2:
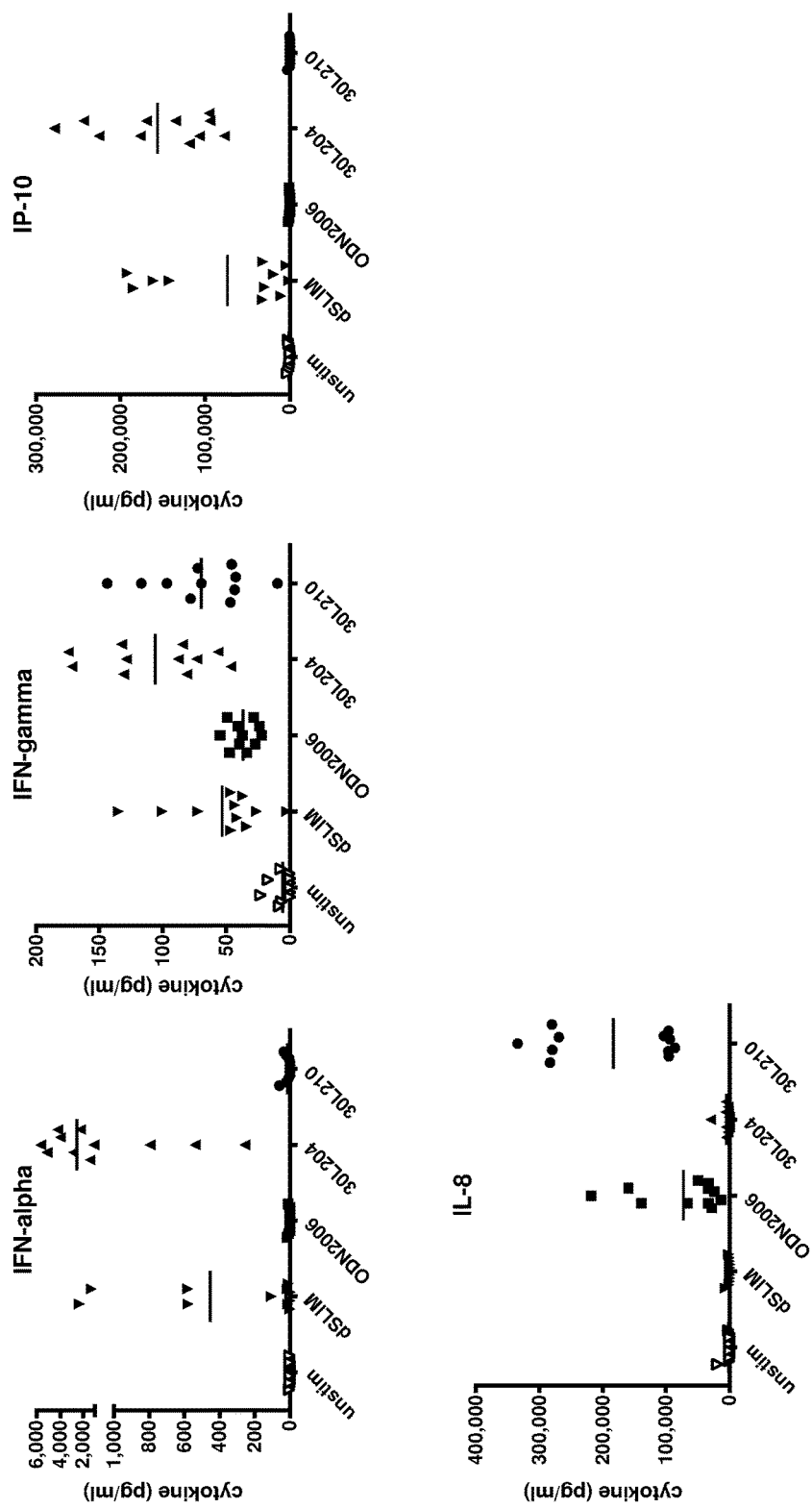

FIG. 2 shows results of stimulating PBMCs with 3 µM of the indicated DNA constructs describes in table 1 above.

The use of DNA constructs having phosphorothioate modified backbones (ODN2006-2 and 30L210) does not lead to a stimulation of IFF-alpha and IP-10. Surprisingly, the DNA construct of the present disclosure (30L204) leads to a significantly enhanced cytokine stimulation of IFN-alpha and IP-10 in comparison to the already known dumbbell-shaped DNA construct of EP 1 196 178 (dSLIM).

IFN-alpha has been known as an antiviral cytokine for many years. It stimulates Th1 cell development, therefore promoting the effects of CG-containing DNA molecules. IFN-alpha also exhibits antitumour activity in mouse and human malignancies and is capable of decreasing the tumourigenicity of transplanted tumour cells, partially by activating cytotoxic T cells and thereby increasing the likelihood of tumour-cell cytolysis. NK cell and macrophage activity, both also important for antitumour cytotoxicity, are also increased by IFN-alpha (Brassard et al., J. Leukoc. Biol. 2002 71: 565-81). Therefore, increasing the amount of IFN-alpha upon stimulation with the DNA constructs of the present disclosure is expected to be beneficial for the treatment of cancer.

IP-10 has been recently demonstrated to be a potent angiostatic protein in vivo. Thus, the induction of IP-10 especially in the treatment of tumour diseases seems to be of advantage too.

The stimulation of IFN-gamma is also increased by the DNA construct of the present disclosure in comparison to the dSLIM. IFN-gamma stimulation seems to be sequence dependent as 30L210 is also stimulating its secretion, but it has to be kept in mind that 30L210 has a phosphorothioate backbone, which might cause severe side effects. Thus, the DNA construct of the present disclosure is beneficial with regard to safety aspects.

IL-8 is stimulated by both DNA constructs having phosphorothioate backbones
(ODN2006-2; 30L210). Thus, the observed effect can be deduced to this modification. The DNA construct of the present disclosure does not increase IL-8 production, which is beneficial.

IL-8 is a proinflammatory cytokine, which is known to mediate the activation and migration of neutrophils into tissue from peripheral blood. The resulting neutrophilic infiltration may be partially responsible for inhibition of tumour growth as has been shown for ovarian cancer (Lee et al., J. Immunol. 2000 164: 2769-75). In addition, IL-8 is also chemotactic for T cells and basophils. Therefore, for treatment or prevention of at least some tumour types it is advantageous to selectively upregulate IL-8 in response to CG-containing DNA constructs. On the other hand it has been established that IL-8 triggers angiogenesis so that the induction of IL-8 secretion might be counterproductive. Thus, the differing degrees of IL-8 induction by the different DNA molecules of the present invention might allow for a tailoring of the molecule to the desired therapeutic effects.

Thus, the specific cytokine pattern induced by a DNA construct of the present disclosure is beneficial for treatment and prevention of distinct tumour types. Obviously, the specific context in which the unmethylated CG motif is incorposrated to TLR9 including the conformation of the DNA construct determines the individual respective stimulation pattern induced in the responding cells.

Figure 3:
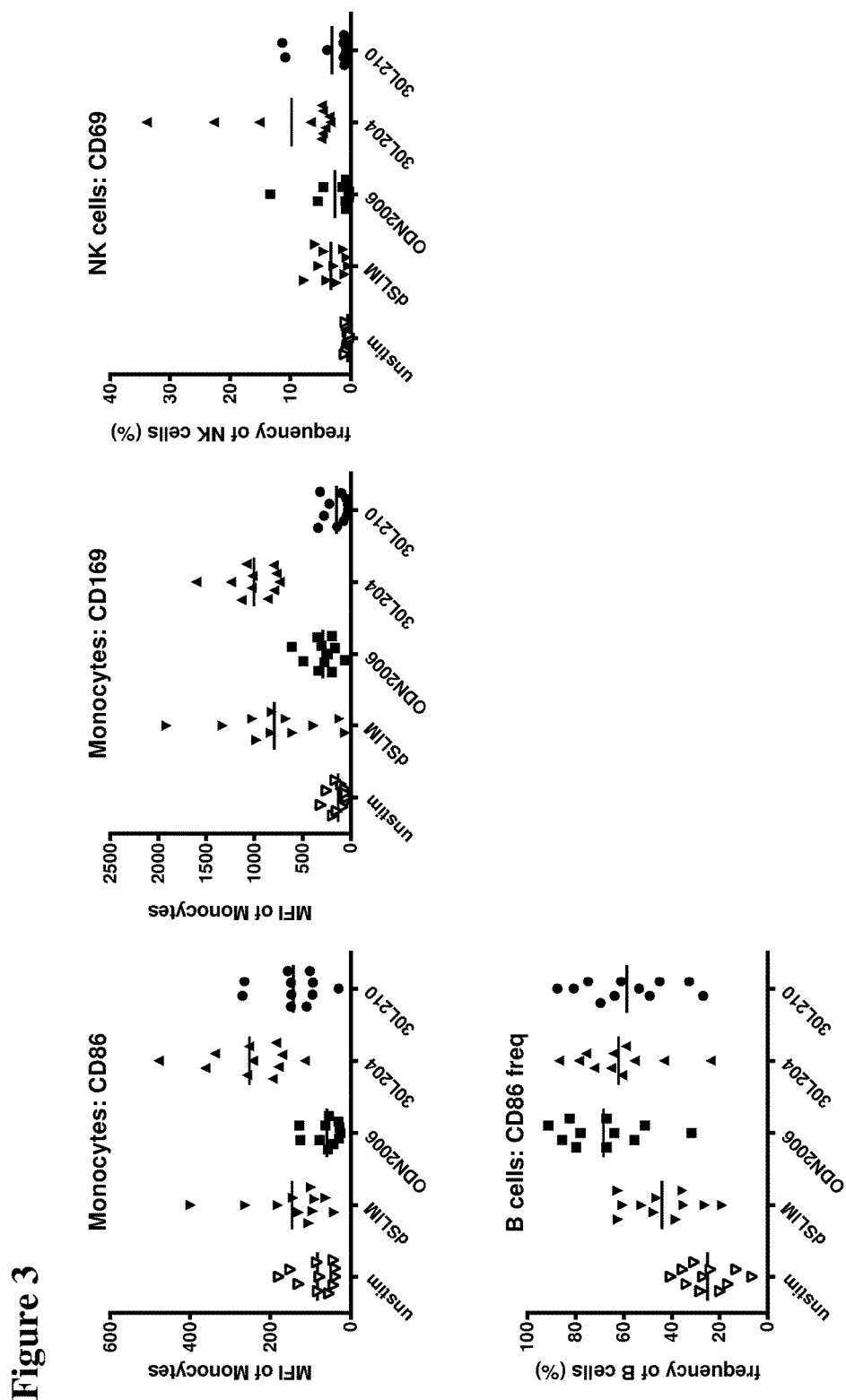

FIG. 3 shows the stimulation of Monocytes with the DNA constructs listed in table 1. The DNA construct of the present disclosure improves the activation of monocytes regarding CD86 and CD169 in comparison to dSLIM and the phosphorothioate protected linear oligo ODN2006-2. Best activation of CD69 is in NK cells is also achieved with the DNA construct of the present invention.

Although the activation of monocytes and NK cells is more or less comparable to the linear ODN2006, again, it has to be kept in mind that this oligo has a phosphorothioate backbone which might cause severe side effects.

The activation of B cells is more or less comparable between the linear ODN2006-2 and the dumbbell-shaped DNA construct of the present disclosure. Comparing the two dumbbell-shaped DNA constructs dSLIM and 30L204 shows that 30L204 is surprisingly a much more potent activator than dSLIM.

In conclusion, the experiments show that the dumbbell-shaped DNA construct of the present disclosure is unexpectedly a better activator of immune cells that the already known dumbbell-shaped DNA construct dSLIM and the linear oligodeoxynucleotide ODN2006 (PROMUNE®). It was surprising that the introduction of the DNA sequence of ODN2006 without phosphorothioate into the single stranded loops of a dumbbell-shaped linear DNA constructs leads to an improvement of of the immunomodulatory potential.

ODN2006 (ProMune®) and dSLIM are both known as potent immunomodulators, The introduction of the phosphorothioate ODN2006 into the single-stranded loops of dSLIM does not result in an efficient immunomodulator (comp. FIG. 1 IFN-alpha and IP-10). The DNA construct of the present disclosure having the sequence of ODN2006 with phosphordiester bonds in the single-stranded loops results in a new construct with an efficiency, which is beyond the mere addition of the effects of ODN2006 and dSLIM. Thus, it has to be concluded that the DNA construct of the present disclosure is a new TLR-9 agonist which can be used for the treatment of cancer or autoimmune diseases by increasing the cytokine secretion of the central anti-cancer cytokine IFN-alpha, the potent angiostatic cytokine IP-10, or IFN-gamma, the key activator of NK-, NKT-, and cytotoxic T-cell responses.

It was also possible to show that the DNA construct of the present disclosure is a strong up-regulator of activation surface markers of relevant cell subpopulations of PBMC including CD80 of pDCs, CD86 of B-cells, CD86 and CD169 of monocytes, CD69 of NK-, NKT- as well as T-cells.

The invention claimed is:

1. A DNA construct for immunomodulation that consists of a partially single-stranded, dumbbell-shaped, covalently closed chain of DNA residues comprising twice the DNA sequence of SEQ ID NO: 1.

2. The construct according to claim 1, wherein at least one nucleotide is modified with a functional group selected from the group consisting of carboxyl, amine, amide, aldimine, ketal, acetal, ester, ether, disulfide, thiol and aldehyde groups.

3. A pharmaceutical composition comprising a DNA construct of claim 1.

4. The pharmaceutical composition according to claim 3, comprising additionally a chemotherapeutic.

5. A vaccine comprising a DNA construct according to claim 1.

* * * * *